US010910090B2

(12) United States Patent
Noda et al.

(10) Patent No.: US 10,910,090 B2
(45) Date of Patent: Feb. 2, 2021

(54) UPDATING TERMINAL IDENTIFICATION INFORMATION BASED ON A COMPARISON WITH TERMINAL INFORMATION IN STORAGE

(71) Applicant: FUJITSU LIMITED, Kawasaki (JP)

(72) Inventors: Kenzo Noda, Naruto (JP); Iori Takeda, Osaka (JP); Hirofumi Mihara, Osaka (JP)

(73) Assignee: FUJITSU LIMITED, Kawasaki (JP)

( * ) Notice: Subject to any disclaimer, the term of this patent is extended or adjusted under 35 U.S.C. 154(b) by 497 days.

(21) Appl. No.: 15/725,797

(22) Filed: Oct. 5, 2017

(65) Prior Publication Data

US 2018/0113981 A1 Apr. 26, 2018

(30) Foreign Application Priority Data

Oct. 20, 2016 (JP) ................................ 2016-206303

(51) Int. Cl.
*G16H 10/60* (2018.01)
*G16H 40/20* (2018.01)
*G16H 40/67* (2018.01)

(52) U.S. Cl.
CPC ............ *G16H 10/60* (2018.01); *G16H 40/20* (2018.01); *G16H 40/67* (2018.01)

(58) Field of Classification Search
CPC ......... G16H 10/60; G16H 40/67; G16H 40/20
(Continued)

(56) References Cited

U.S. PATENT DOCUMENTS

2004/0049413 A1* 3/2004 Momma ................ G06Q 10/02 705/5
2010/0169879 A1* 7/2010 Takeda ...................... G06F 8/60 717/177
(Continued)

FOREIGN PATENT DOCUMENTS

JP 4-155462 5/1992
JP 2010-34915 A 2/2010
(Continued)

OTHER PUBLICATIONS

Japanese Office Action dated Oct. 6, 2020 for corresponding Japanese Patent Application No. 2016-206303, with English Translation, 8 pages.

*Primary Examiner* — David P Zarka
(74) *Attorney, Agent, or Firm* — Fujitsu Patent Center

(57) ABSTRACT

A medium storing a program that causes a computer to execute a process includes receiving first pieces of terminal identification information and a request for updating second pieces of terminal identification information included in management targets to the first pieces of terminal identification information, comparing the second pieces of terminal identification information with the first pieces of terminal identification information, transmitting information including at least one of a first number of terminals to be excluded from the management targets by executing a update regarding the request, a second number of terminals to be added to the management targets by executing the update, and a third number of terminals that are included in the management targets before and after executing the update, and when receiving an instruction to execute the update regarding the request, updating the second pieces of terminal identification information to the first pieces of terminal identification information.

14 Claims, 13 Drawing Sheets

(58) Field of Classification Search
USPC .......................................................... 709/223
See application file for complete search history.

(56) References Cited

U.S. PATENT DOCUMENTS

2010/0223384 A1* 9/2010 Takeda ...................... G06F 8/65
709/226
2010/0251387 A1* 9/2010 Takeda .................... G06F 21/10
726/29
2012/0072587 A1* 3/2012 Nishiyama .......... H04L 41/0266
709/224

FOREIGN PATENT DOCUMENTS

JP 2012-84120 4/2012
JP 2015-87787 A 5/2015

* cited by examiner

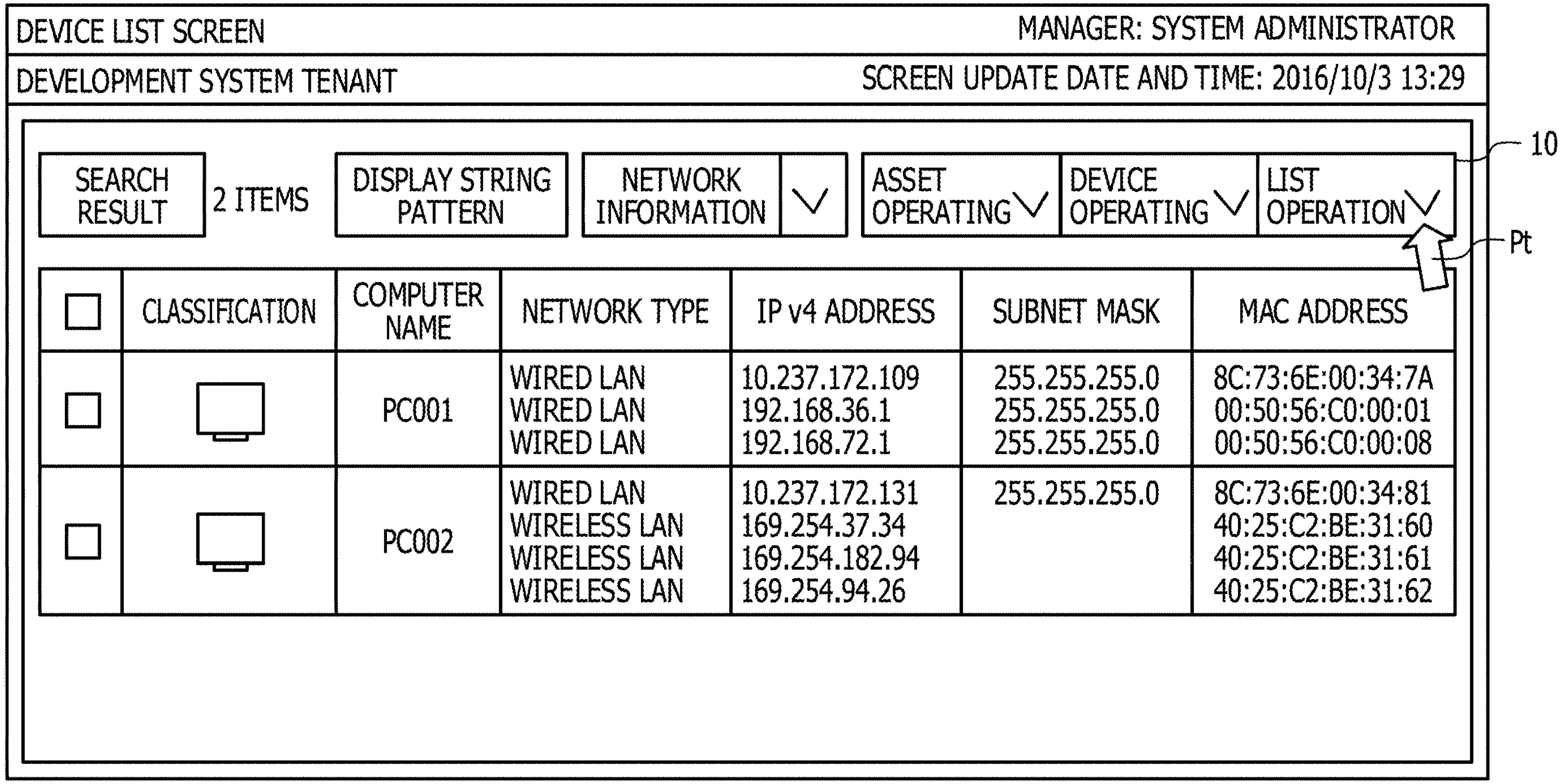

FIG. 4

| DEVICE LIST SCREEN | | | | | | | MANAGER: SYSTEM ADMINISTRATOR | |
|---|---|---|---|---|---|---|---|---|
| DEVELOPMENT SYSTEM TENANT | | | | | | | SCREEN UPDATE DATE AND TIME: 2016/10/3 13:29 | |
| SEARCH RESULT | 2 ITEMS | DISPLAY STRING PATTERN | NETWORK INFORMATION ∨ | | ASSET OPERATING ∨ | DEVICE OPERATING ∨ | LIST OPERATION ∨ | |
| ☐ | CLASSIFICATION | COMPUTER NAME | NETWORK TYPE | IP v4 ADDRESS | SUBNET MASK | | MAC ADDRESS | |
| ☐ | 🖥 | PC001 | WIRED LAN<br>WIRED LAN<br>WIRED LAN | 10.237.172.109<br>192.168.36.1<br>192.168.72.1 | 255.255.255.0<br>255.255.255.0<br>255.255.255.0 | | 8C:73:6E:00:34:7A<br>00:50:56:C0:00:01<br>00:50:56:C0:00:08 | |
| ☐ | 🖥 | PC002 | WIRED LAN<br>WIRELESS LAN<br>WIRELESS LAN<br>WIRELESS LAN | 10.237.172.131<br>169.254.37.34<br>169.254.182.94<br>169.254.94.26 | 255.255.255.0 | | 8C:73:6E:00:34:81<br>40:25:C2:BE:31:60<br>40:25:C2:BE:31:61<br>40:25:C2:BE:31:62 | |

10
Pt

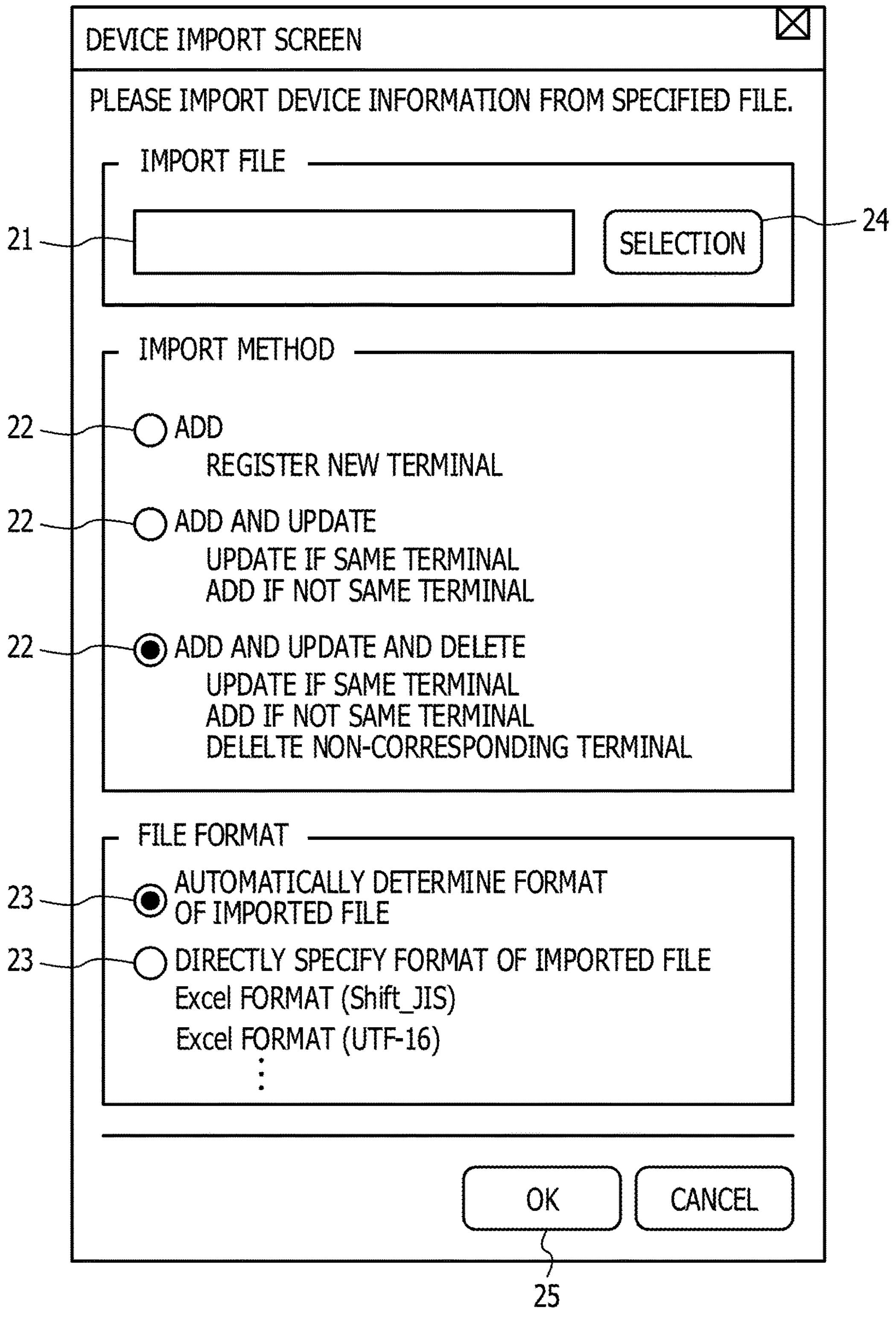

FIG. 6

DEVICE IMPORT SCREEN

PLEASE IMPORT DEVICE INFORMATION FROM SPECIFIED FILE.

IMPORT FILE

21 — [ ]    [ SELECTION ] — 24

IMPORT METHOD

22 — ○ ADD
   REGISTER NEW TERMINAL

22 — ○ ADD AND UPDATE
   UPDATE IF SAME TERMINAL
   ADD IF NOT SAME TERMINAL

22 — ● ADD AND UPDATE AND DELETE
   UPDATE IF SAME TERMINAL
   ADD IF NOT SAME TERMINAL
   DELELTE NON-CORRESPONDING TERMINAL

FILE FORMAT

23 — ● AUTOMATICALLY DETERMINE FORMAT OF IMPORTED FILE

23 — ○ DIRECTLY SPECIFY FORMAT OF IMPORTED FILE
   Excel FORMAT (Shift_JIS)
   Excel FORMAT (UTF-16)
   ⋮

[ OK ]  [ CANCEL ]

| IMPORT FILE | |
|---|---|
| ROW | FILED NAME |
| 1 | FILE VERSION |
| 2 | MULTI BOOTING |
| 3 | FUNCTIONAL KEY |
| 4 | ··· |
| 5 | TERMINAL ID |
| : | : |
| 11 | COMPUTER NAME |
| : | : |
| 18 | NETWORK TYPE |
| 19 | MAC ADDRESS |
| 20 | IPv4 ADDRESS |
| 21 | SUBNET MASK |
| 22 | GATEWAY |
| : | : |

HEADER SECTION (rows 1–4)

DETAIL SECTION (rows 5 onward)

NETWORK INFORMATION (rows 18–22)

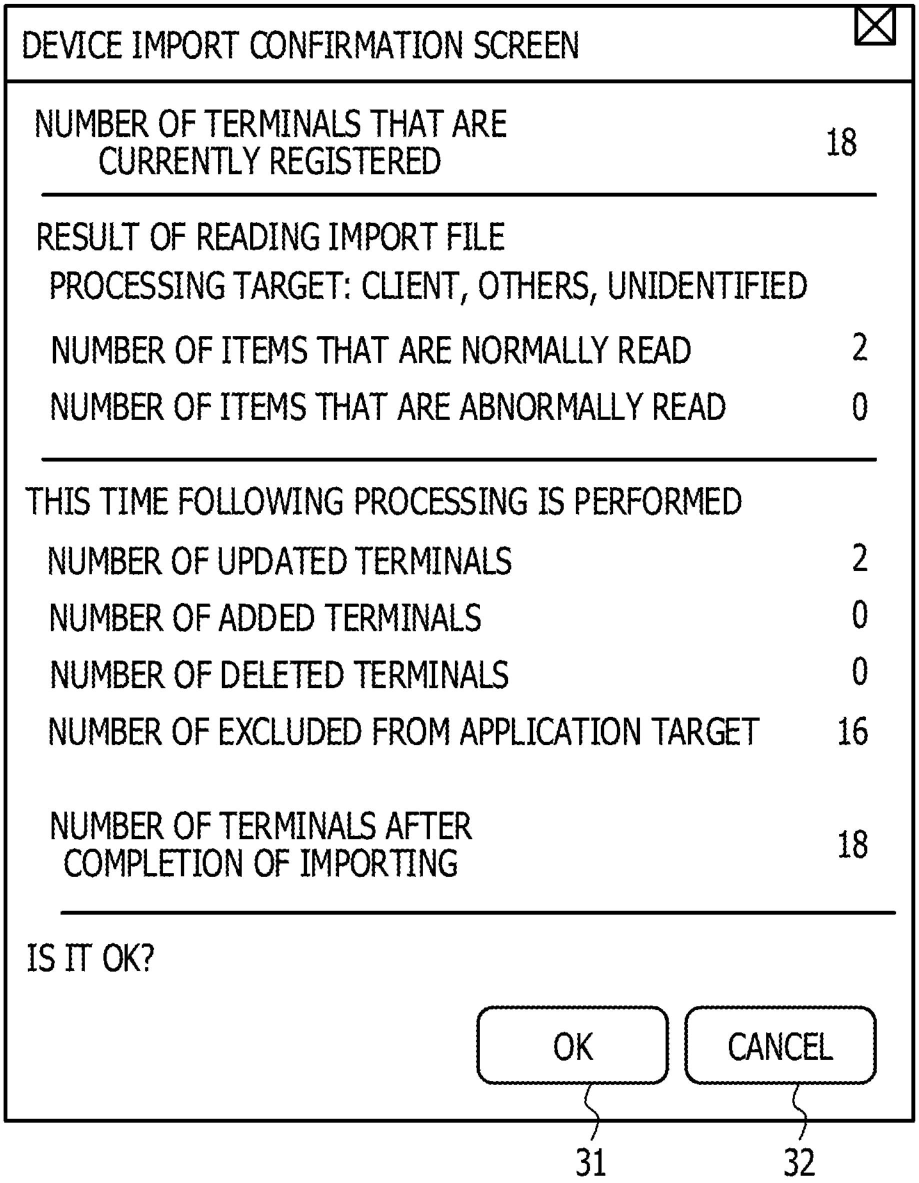

FIG. 13

| DEVICE IMPORT CONFIRMATION SCREEN | ☒ |
|---|---|
| NUMBER OF TERMINALS THAT ARE CURRENTLY REGISTERED | 18 |

RESULT OF READING IMPORT FILE
  PROCESSING TARGET: CLIENT, OTHERS, UNIDENTIFIED

| NUMBER OF ITEMS THAT ARE NORMALLY READ | 2 |
|---|---|
| NUMBER OF ITEMS THAT ARE ABNORMALLY READ | 0 |

THIS TIME FOLLOWING PROCESSING IS PERFORMED

| NUMBER OF UPDATED TERMINALS | 2 |
|---|---|
| NUMBER OF ADDED TERMINALS | 0 |
| NUMBER OF DELETED TERMINALS | 0 |
| NUMBER OF EXCLUDED FROM APPLICATION TARGET | 16 |
| NUMBER OF TERMINALS AFTER COMPLETION OF IMPORTING | 18 |

IS IT OK?

[ OK ] (31)  [ CANCEL ] (32)

UPDATING TERMINAL IDENTIFICATION INFORMATION BASED ON A COMPARISON WITH TERMINAL INFORMATION IN STORAGE

CROSS-REFERENCE TO RELATED APPLICATION

This application is based upon and claims the benefit of priority of the prior Japanese Patent Application No. 2016-206303, filed on Oct. 20, 2016, the entire contents of which are incorporated herein by reference.

FIELD

The embodiment discussed herein is related to a technology for updating information.

BACKGROUND

A device management apparatus is known that acquires device information by periodically performing polling on a management target device according to an internet protocol (IP) address and registers the acquired device information in management information for performing device management. In addition, the device management apparatus is also known that, desirably, updates the management information to the latest information in a case where a device is moved or replaced (see, for example, Japanese Laid-open Patent Publication No. 2012-084120).

SUMMARY

According to an aspect of the invention, a medium storing a program that causes a computer to execute a process includes receiving first pieces of terminal identification information and a request for updating second pieces of terminal identification information included in management targets to the first pieces of terminal identification information, comparing the second pieces of terminal identification information with the first pieces of terminal identification information, transmitting information including at least one of a first number of terminals to be excluded from the management targets by executing a update regarding the request, a second number of terminals to be added to the management targets by executing the update, and a third number of terminals that are included in the management targets before and after executing the update, and when receiving an instruction to execute the update regarding the request, updating the second pieces of terminal identification information to the first pieces of terminal identification information.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 is an example of a device list screen;

FIG. 6 is an example of a device import screen;

FIG. 10 is an example of a file format of an import file;

FIG. 13 is an example of a device import confirmation screen.

DESCRIPTION OF EMBODIMENT

In the related art, when management information is erroneously updated, an operation of returning to the state before the update may occur, which may be troublesome.

Hereinafter, an embodiment of implementing the embodiment will be described with reference to the drawings.

Figure 1:
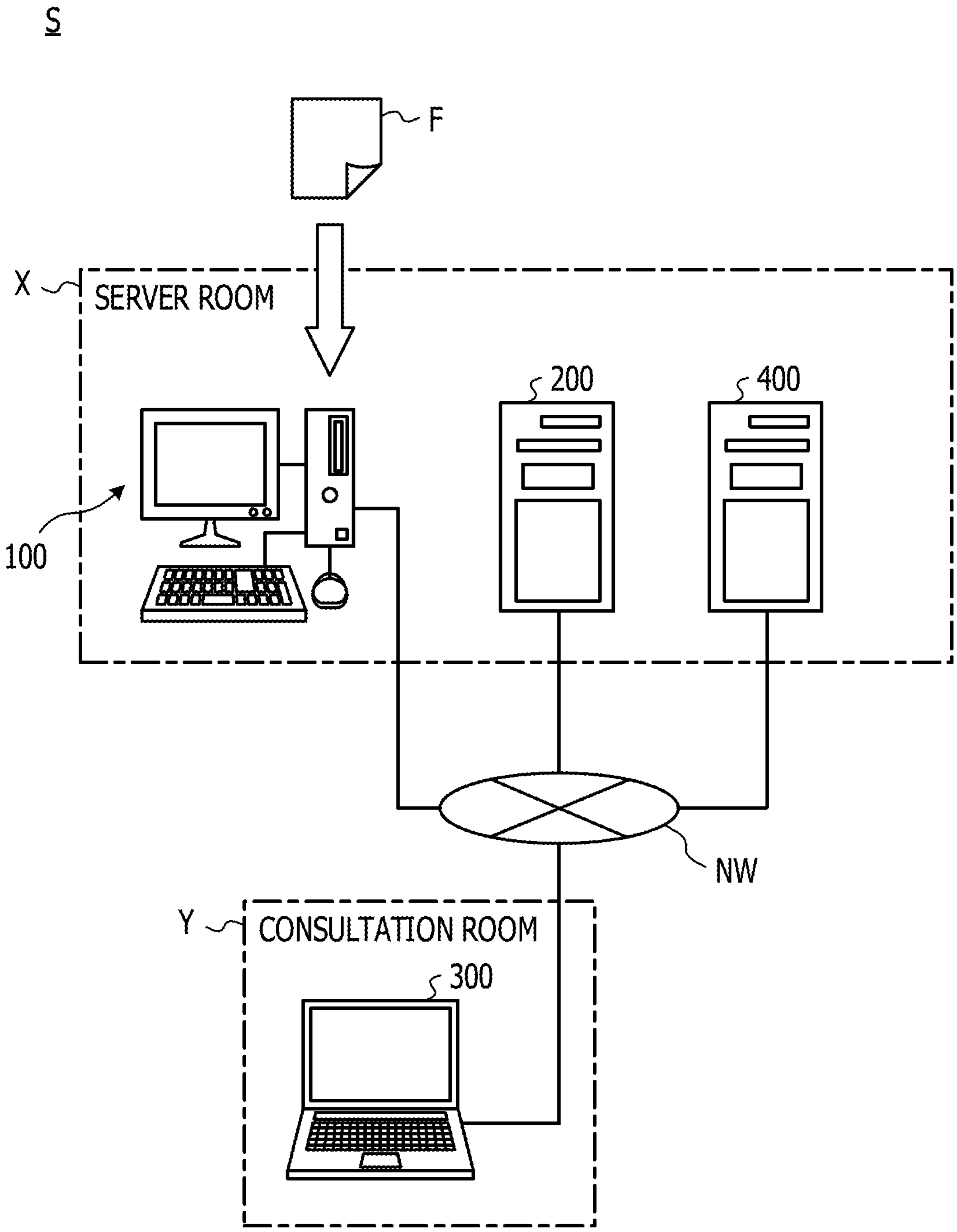
FIG. 1 is a diagram illustrating an example of an information processing system.

FIG. 1 is a diagram illustrating an example of an information processing system S. The information processing system S includes a management terminal 100 and an information update server 200 as an information update apparatus. An electronic medical chart terminal 300 or an electronic medical chart server 400 may be included as a component of an information processing system S. The management terminal 100, the information update server 200, the electronic medical chart terminal 300, and the electronic medical chart server 400 are connected to one another via a communication network NW. An example of the communication network NW includes a wired or wireless Local Area Network (LAN). Although FIG. 1 illustrates a Personal Computer (PC) as an example of the management terminal 100 and the electronic medical chart terminal 300, the management terminal 100 and the electronic medical chart terminal 300 are not limited to the PC, but may be, for example, a smart device such as a tablet terminal.

The management terminal 100, the information update server 200 and the electronic medical chart server 400 are installed in, for example, a server room X of a medical institution. Meanwhile, the electronic medical chart terminal 300 is installed in, for example, a consultation room Y of the medical institution. The electronic medical chart terminal 300 is operated by a medical staff such as a doctor or a nurse. The electronic medical chart terminal 300 accesses the electronic medical chart server 400 based on an operation by the medical staff, acquires information regarding medical treatment from the electronic medical chart server 400, and displays the acquired information.

The information update server 200 stores device information for managing a plurality of electronic medical chart terminals 300 installed in the medical institution. Although described below in detail, the device information includes a terminal ID and a computer name for identifying the electronic medical chart terminal 300, an Internet Protocol (IP) and a Media Access Control (MAC) address assigned to the electronic medical chart terminal 300, and a network type for identifying whether a connection form of the electronic medical chart terminal 300 is a wired LAN or a wireless LAN, and the like.

The management terminal 100 is a terminal apparatus used by an administrator who manages device information. The management terminal 100 stores an electronic file (hereinafter, referred to as an import file) F imported from the outside of the medical institution into the medical institution. The import file F is a file used when the above mentioned device information is updated, and is created using macro processing, or the like. The import file F is, for example, imported with being stored in a Universal Serial Bus (USB) memory, or is imported through a communication network NW.

When the import file F is uploaded from the management terminal 100 to the information update server 200 and the information of the electronic medical chart terminal 300 included in the import file F is not present in the device information, the information of the electronic medical chart terminal 300 is added to the device information. In contrast, when the information of the electronic medical chart terminal 300 included in the import file F is present in the device information, the information of the electronic medical chart terminal 300 is rewritten. On the other hand, when the information of the electronic medical chart terminal 300 is not included in the import file F and the information of the electronic medical chart terminal 300 is present in the device information, the information is deleted from the device information.

Hereinafter, the information processing system S will be described in detail with reference to the drawings.

Figure 2:
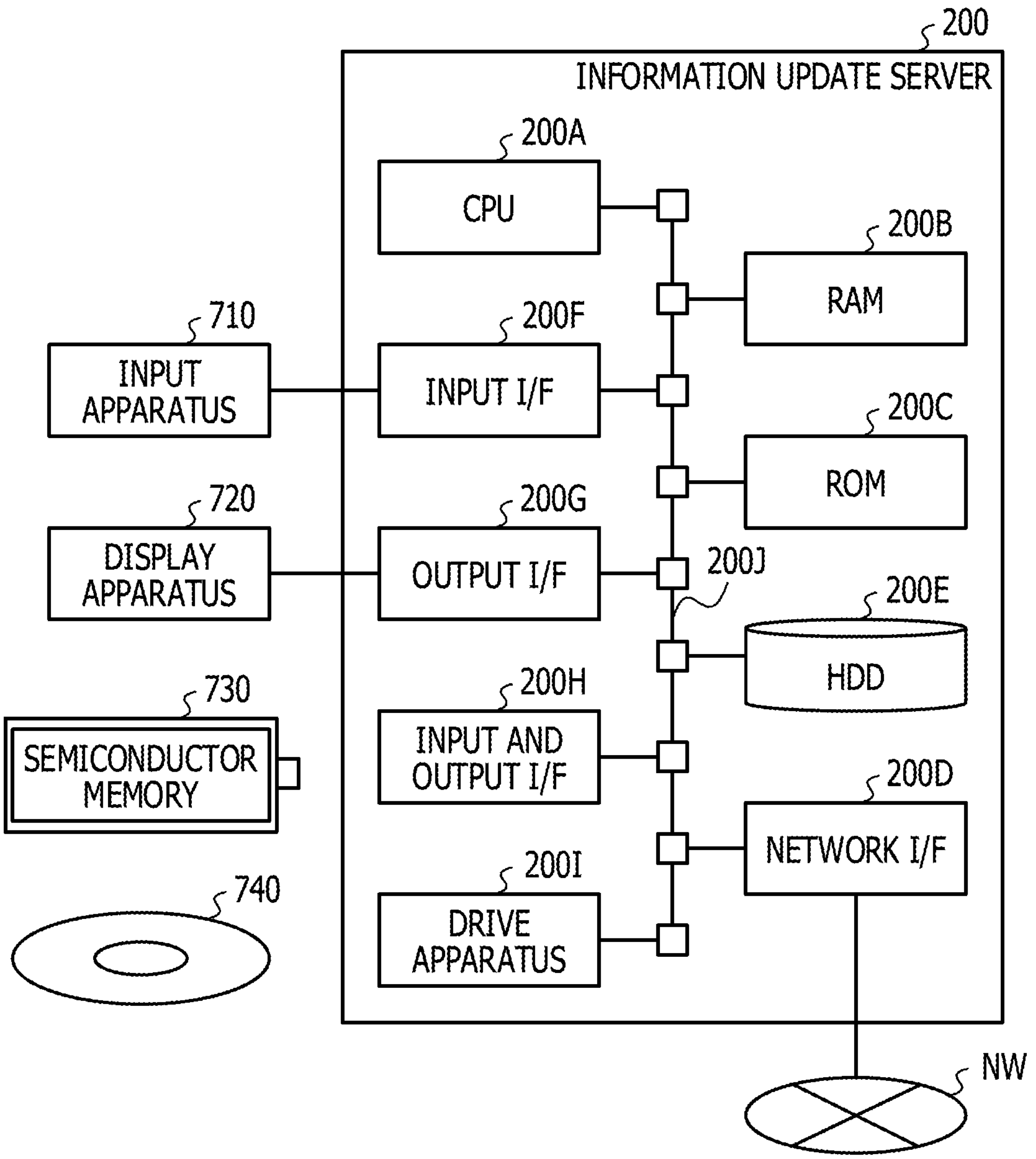
FIG. 2 is an example of a hardware configuration of an information update server.

FIG. 2 illustrates an example of a hardware configuration of the information update server 200. Since the management terminal 100, the electronic medical chart terminal 300, and the electronic medical chart server 400 are basically of the same configuration as that of the information update server 200, the description thereof will be omitted.

The information update server 200 includes at least a Central Processing Unit (CPU) 200A, a Random Access Memory (RAM) 200B, a Read Only Memory (ROM) 200C, and a network interface (I/F) 200D. The information update server 200 may include at least one of a Hard Disk Drive (HDD) 200E, an input I/F 200F, an output I/F 200G, an input/output I/F 200H, and a drive apparatus 200I as appropriate. The CPU 200A to the drive apparatus 200I are connected to one another through an internal bus 200J. At least the CPU 200A and the RAM 200B cooperate to build a computer.

An input apparatus 710 is connected to the input I/F 200F. An example of the input apparatus 710 includes a keyboard or a mouse.

A display apparatus 720 is connected to the output I/F 200G. An example of the display apparatus 720 includes a liquid crystal display.

A semiconductor memory 730 is connected to the input/output I/F 200H. An example of the semiconductor memory 730 includes a USB memory or a flash memory. The input/output I/F F200H reads a program or data stored in the semiconductor memory 730.

The input/output I/F 200F and the input/output I/F 200H have USB ports, for example. The output I/F 200G has a display port, for example.

A portable recording medium 740 is inserted into the drive apparatus 200I. An example of the portable recording medium 740 includes a removable disk such as a Compact Disc (CD)-ROM or Digital Versatile Disc (DVD). The drive apparatus 200I reads a program or data recorded in the portable recording medium 740.

The network I/F 200D includes, for example, a port and a Physical Layer Chip (PHY chip). The information update server 200 is connected to the communication network NW through the network I/F 200D.

In the RAM 200B described above, a program stored in the ROM 200C or the HDD 200E is stored by the CPU 200A. In the RAM 200B, a program recorded in the portable recording medium 740 is stored by the CPU 200A. The CPU 200A executes the stored program, such that the information update server 200 carries out various functions described below and executes various kinds of processing described below. It is noted that the program may be operated in accordance with a flowchart described below.

Figure 3:
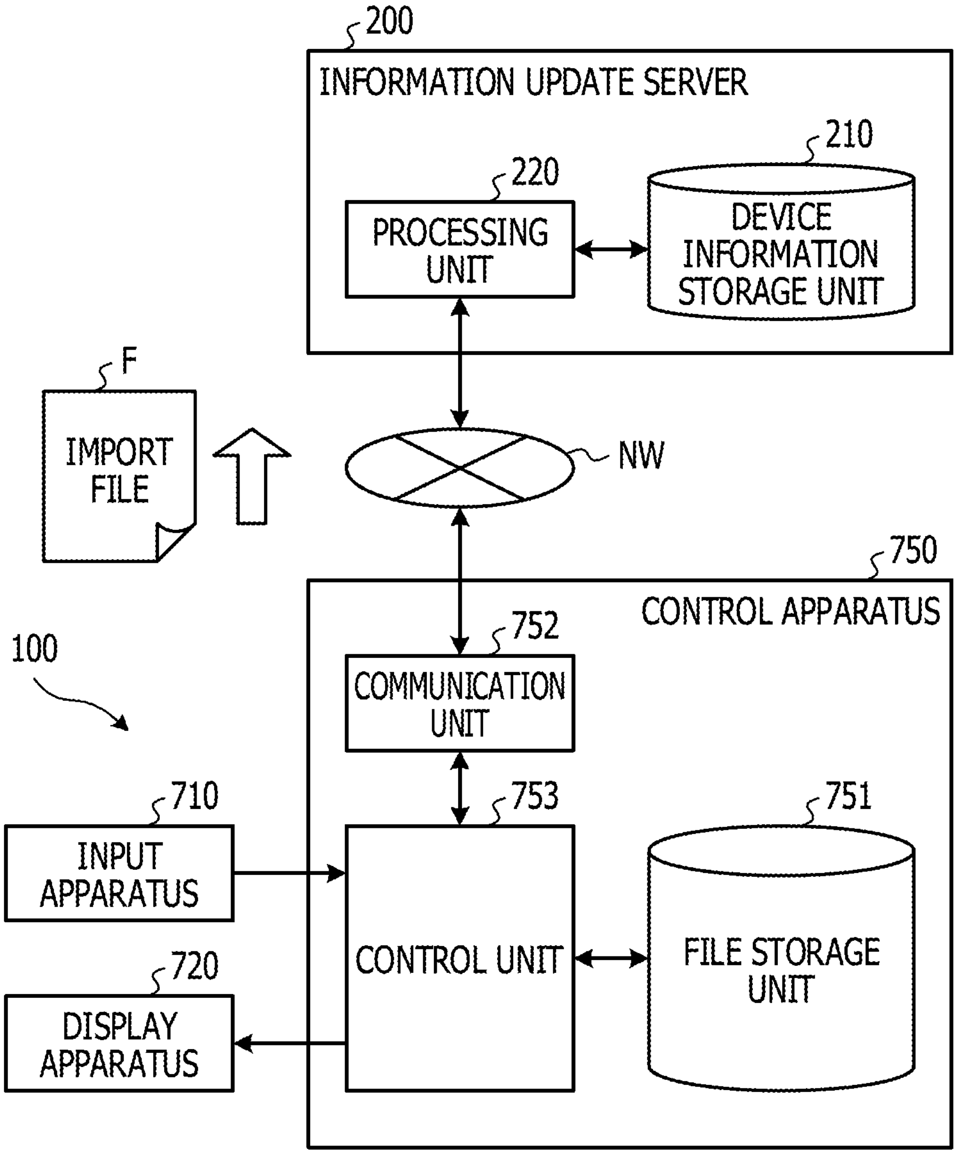
FIG. 3 is an example of a functional block diagram of a management terminal and the information update server.

FIG. 3 illustrates an example of a functional block diagram of the management terminal 100 and the information update server 200.

First, the management terminal 100 will be described. As illustrated in FIG. 3, the management terminal 100 includes the input apparatus 710, the display apparatus 720, and a control apparatus 750. In particular, the control apparatus 750 includes a file storage unit 751, a communication unit 752, and a control unit 753. The file storage unit 751 is implemented by, for example, the HDD 200E described above. The communication unit 752 is implemented by, for example, the network I/F 200D described above. The control unit 753 is implemented by, for example, the CPU 200A and the RAM 200B described above.

The file storage unit 751 stores the import file F. For example, when the USB memory is connected to the control apparatus 750, the control unit 753 acquires the import file F stored in the USB memory, and stores the acquired import file F in the file storage unit 751. For example, when the communication unit 752 receives the import file F, the control unit 753 stores the import file F received by the communication unit 752 in the file storage unit 751.

The communication unit 752 controls communication between the management terminal 100 and the information update server 200. For example, the communication unit 752 receives various kinds of information (for example, screen information and the like) transmitted from the information update server 200. For example, the communication unit 752 transmits various kinds of information (for example, the import file F, and the like) to the information update server 200.

The control unit 753 controls the overall operation of the management terminal 100. For example, when an instruction input from the input apparatus 710 is received, the control unit 753 changes the display content of the display apparatus 720 according to the content of the instruction or causes the communication unit 752 to transmit various information. For example, when the communication unit 752 receives information transmitted from the information update server 200, the control unit 753 changes the display content of the display apparatus 720 according to the received information, or stores the information in the file storage unit 751. In addition, the control unit 753 executes various kinds of information processing.

Next, the information update server 200 will be described. As illustrated in FIG. 3, the information update server 200 includes a device information storage unit 210 and a processing unit 220.

The device information storage unit 210 is implemented by, for example, the HDD 200E described above. The processing unit 220 is implemented by, for example, the CPU 200A, the RAM 200B and the network I/F 200D described above.

The device information storage unit 210 stores device information as the management target. In addition to the terminal ID, the computer name, the IP address, the MAC address, or the network type described above, the device information includes, for example, a subnet mask, an address of a gateway connected to the electronic medical chart terminal 300, or the like, as components. A plurality of electronic chart terminals 300 installed in a medical institution are managed by the device information.

The processing unit 220 executes various kinds of information processing. For example, when the processing unit 220 receives information containing a request for a predetermined screen (hereinafter, referred as a device list screen) including a list of device information from the management terminal 100, the processing unit 220 acquires device information from the device information storage unit 210. Then, the processing unit 220 transmits the screen information including the list of the acquired device information to the management terminal 100. When the management terminal 100 receives the screen information, the device list screen is displayed based on the screen information. For example, when the processing unit 220 receives the import file F from the management terminal 100, the processing unit 220 compares various components included in the import file F with various components included in the device information, and transmits the screen information of the screen corresponding to the comparison result (hereinafter, referred to as a device import confirmation screen) to the management terminal 100. When the management terminal 100 receives the screen information, the device import confirmation screen is displayed based on the screen information. For example, when the processing unit 220 receives an instruction to update the device information from the management terminal 100, the processing unit 220 updates the device information stored in the device information storage unit 210 according to the received instruction.

Figure 5:
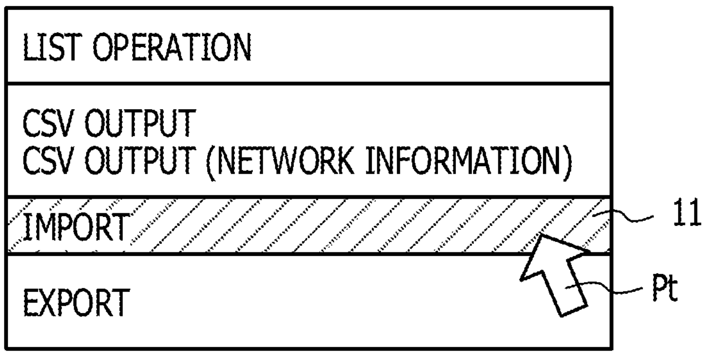
FIG. 5 is an example of a diagram illustrating the development of a list operation.

Next, with reference to FIG. 4 to FIG. 6, respective operations related to pre-processing of the management terminal 100 and the information update server 200 will be described.

FIG. 4 is an example of the device list screen. FIG. 5 is an example of a diagram illustrating the development of a list operation. FIG. 6 is an example of a device import screen. First, when the control unit 753 of the management terminal 100 receives an instruction to request the device list screen from the input apparatus 710, the control unit 753 generates information containing the request for the device list screen. When the control unit 753 generates the information containing the request for the device list screen, the communication unit 752 transmits the information to the information update server 200.

When the information containing the request for the device list screen is received, the processing unit 220 of the information update server 200 transmits the screen information of the device list screen to the management terminal 100. Therefore, as illustrated in FIG. 4, the management terminal 100 displays the device list screen. On the device list screen, a part of the device information stored in the device information storage unit 210 appears. For example, in the field of the computer name, a name of the electronic terminal 300 appears. For example, in the IPv4 address field, the IP address assigned to the electronic terminal 300 appears. Accordingly, the administrator can confirm various kinds of information regarding the electronic chart terminal 300 managed by the information update server 200.

Next, when the control unit 753 receives an instruction to request the device import screen from the input apparatus 710, the control unit 753 generates the information containing the request for the device import screen. More specifically, as illustrated in FIG. 4, when a specific image 10 (for example, a list operation button) on the device list screen is indicated by a pointer Pt, the control unit 753 receives the indication and develops the image 10 as illustrated in FIG. 5, and displays a plurality of selection fields on the display apparatus 720. Further, as illustrated in FIG. 5, when a specific selection field 11 is indicated by the pointer Pt, the control unit 753 receives the indication, and the control unit 753 generates information containing the request for the device import screen. When the control unit 753 generates the information containing the request for the device import screen, the communication unit 752 transmits the information to the information update server 200.

When the information containing the request for the device import screen is received, the processing unit 220 of the information update server 200 transmits screen information of the device import screen to the management terminal 100. As a result, as illustrated in FIG. 6, the management terminal 100 displays the device import screen. On the device import screen, a selecting column 21 for selecting an import file, a plurality of selecting options 22 for selecting an import method, and a plurality of selecting options 23 for selecting a file format appear. Accordingly, the administrator can select the import file F, the import method, and the file format to be uploaded to the information update server 200.

Next, with reference to FIG. 7 and FIG. 8, respective operations related to main processing of the management terminal 100 and the information update server 200 will be described.

Figure 7:
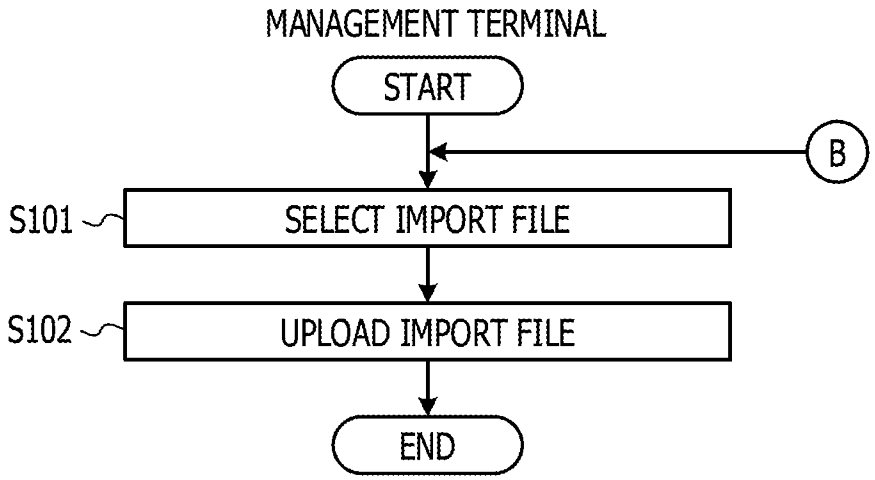
FIG. 7 is a flowchart illustrating an example of operations of the management terminal.

FIG. 7 is a flowchart illustrating an example of operations of the management terminal 100.

First, as illustrated in FIG. 7, the control unit 753 selects the import file F (step S101). More specifically, when a specific image 24 (for example, a selection button) on the device import screen illustrated in FIG. 6 is indicated, the control unit 753 displays a plurality of file names specifying the import file F on the display apparatus 720. Further, when the control unit 753 detects an instruction to select any one of a plurality of displayed file names, the control unit 753 displays the selected file name in the selecting column 21. As a result, the control unit 753 completes the selection of the import file F. Also, when specific selecting options 22, 23 on the device import screen are indicated, the control unit 753 changes display modes of the indicated specific selecting options 22, 23. Thus, the control unit 753 completes the importing method of the importing file F and specification of the file format.

Next, the control unit 753 uploads the import file F (step S102). More specifically, when a specific image 25 (for example, an OK button) is indicated on the device import screen illustrated in FIG. 6, the control unit 753 uploads, to the information update server 200, the file format specified by the import file F specified by the file name displayed in the selecting column 21 and the import method and import format specified by the selecting options 22, 23, together with the instruction to update the device information.

Figure 8:
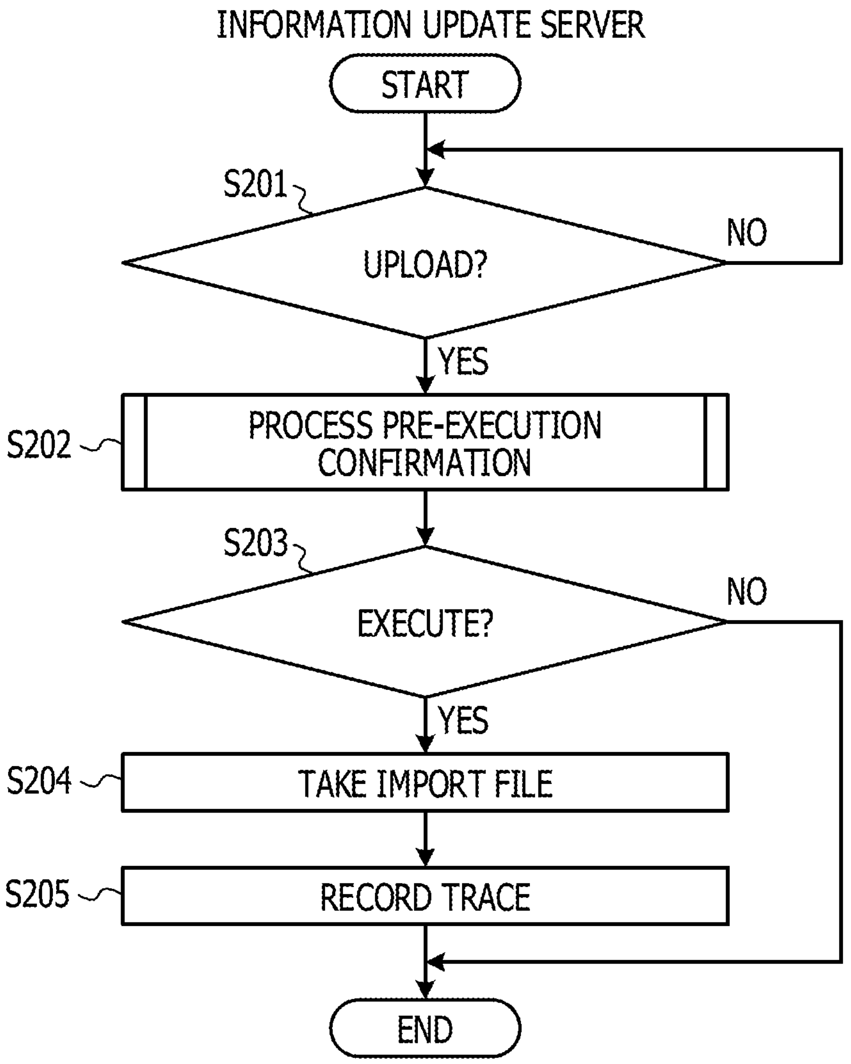
FIG. 8 is a flowchart illustrating an example of operations of the information update server.

FIG. 8 is a flowchart illustrating an example of operations of the information update server 200. The processing unit 220 of the information update server 200 waits until the import file F is uploaded (step S201: NO). When the processing unit detects that the import file F has been uploaded (step S201: YES), the processing unit 220 executes pre-execution confirmation processing (step S202). The pre-execution confirmation processing is a processing for causing the administrator to confirm update of the device information by the import file F before the update is executed. The pre-execution confirmation processing will be described below in detail.

When the processing of step S202 is completed, then the processing unit 220 determines whether or not the instruction to update the device information is received (step S203). For example, in a case where the processing unit 220 receives an instruction not to update the device information (step S203: NO), the processing ends. On the other hand, in a case where the processing unit 220 receives the instruction to update the device information (step S203: YES), the processing unit 220 takes in the import file F (step S204). That is, the processing unit 220 updates the device information with the import file F. When the processing of step S204 is completed, the processing unit 220 records a trace (trail) (step S205). More specifically, the processing unit 220 holds the processing process of step S204, and records the processing process in the device information storage unit 210 or a storage unit other than the device information storage unit 210. By confirming the recorded trace, the administrator can identify what kind of update has been performed on the device information.

Next, with reference to FIG. 9 to FIG. 13, the above-mentioned pre-execution confirmation processing will be described in detail.

Figure 9:
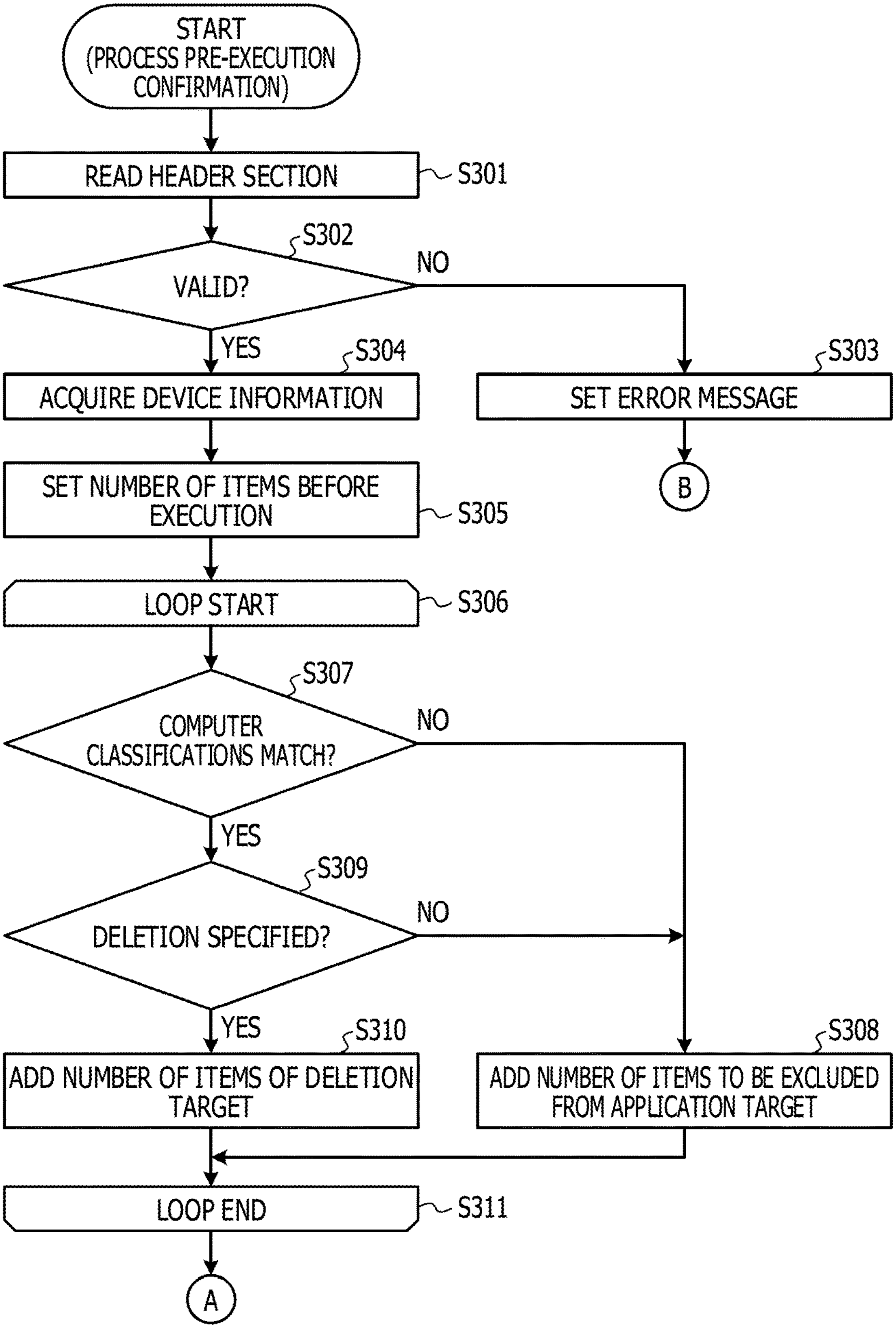
FIG. 9 is a flowchart illustrating an example of a pre-execution confirmation processing (first processing)
Figure 11:
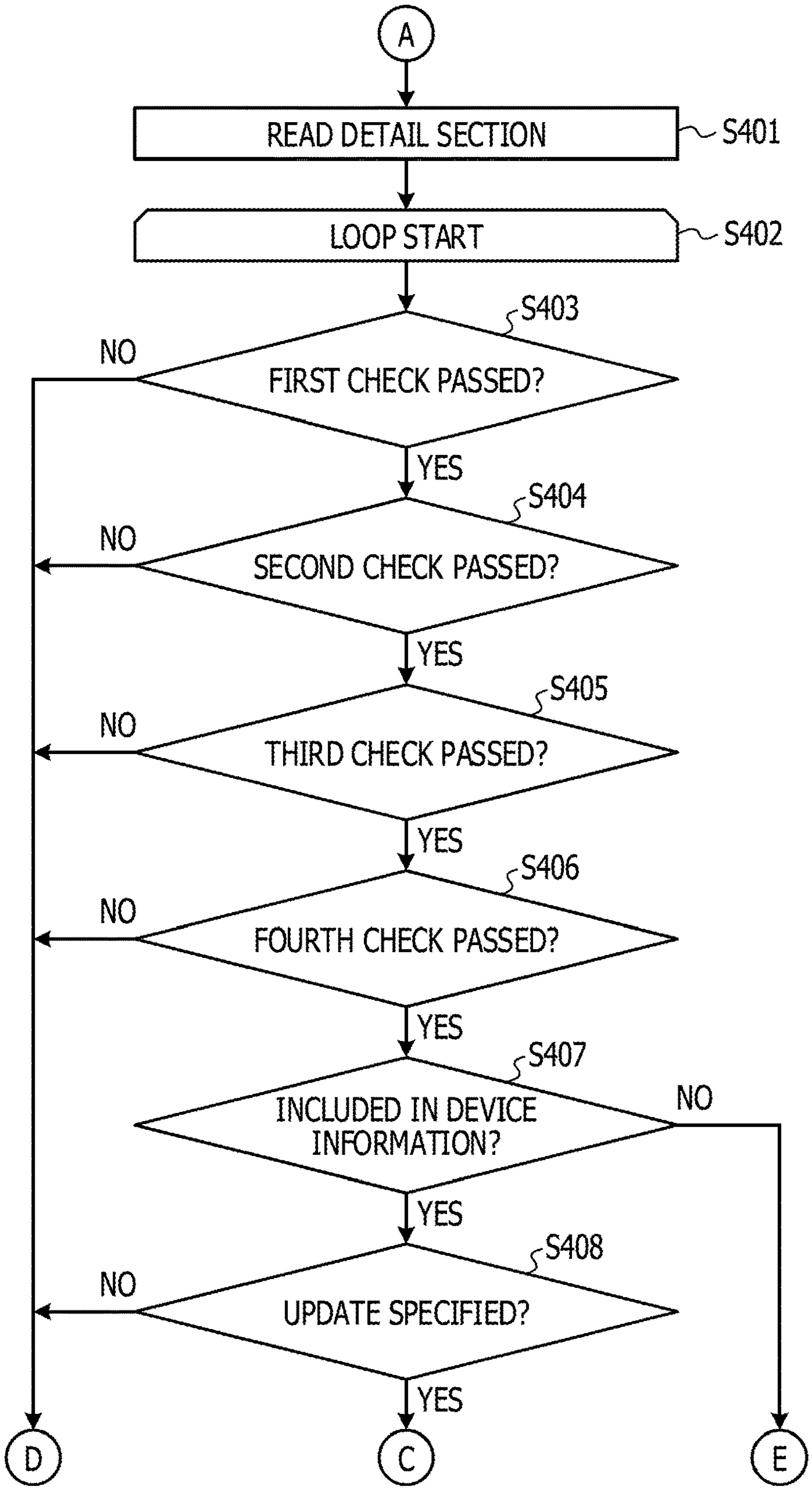
FIG. 11 is a flowchart illustrating another example of the pre-execution confirmation processing (second processing)
Figure 12:
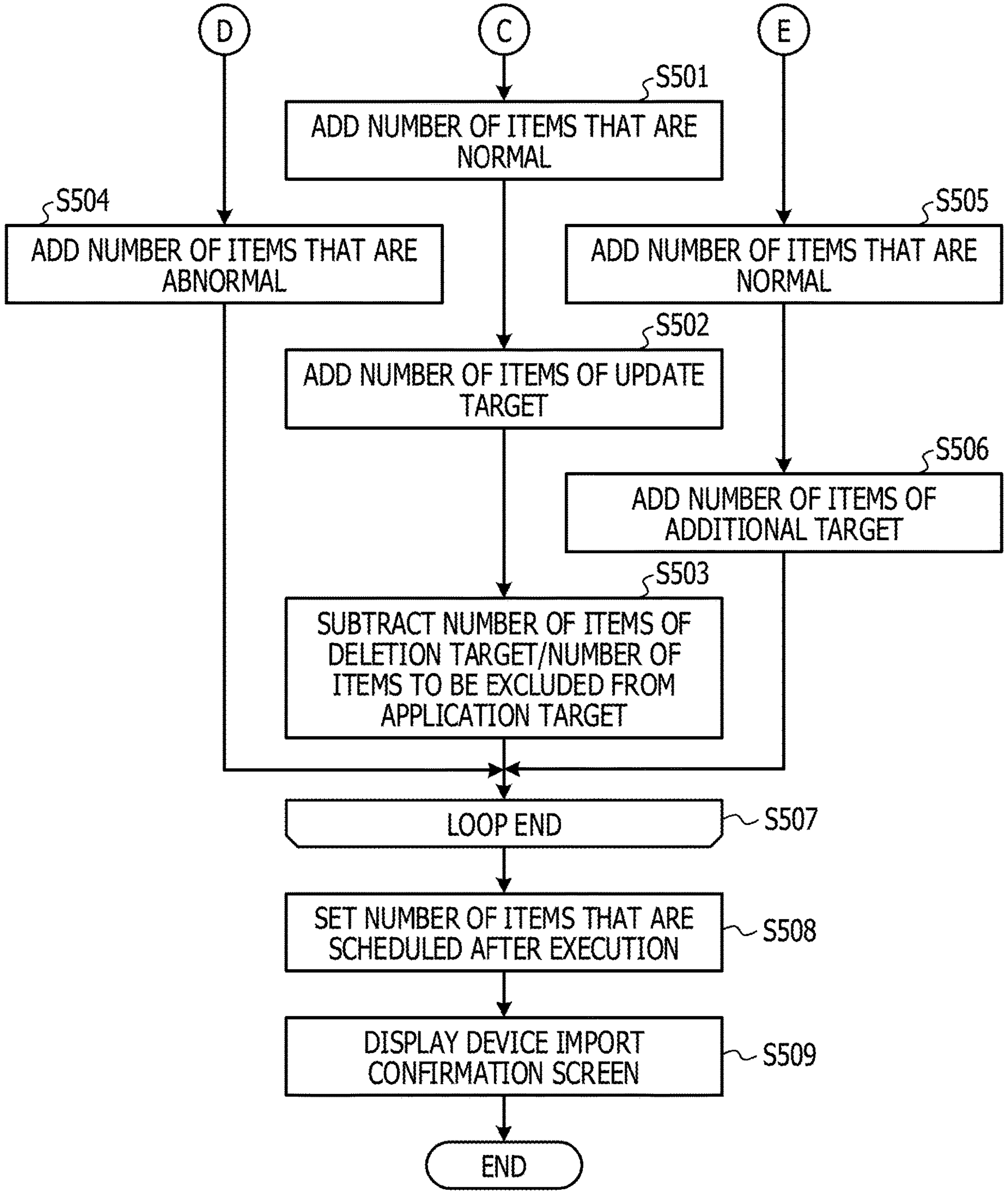
FIG. 12 is a flowchart illustrating still another example of the pre-execution confirmation processing (third processing)

FIG. 9 is a flowchart illustrating an example of the pre-execution confirmation processing (first processing). FIG. 10 is an example of a file format of the import file F. FIG. 11 is a flowchart illustrating another example of the pre-execution confirmation processing (second processing). FIG. 12 is a flowchart illustrating yet another example of the pre-execution confirmation processing (third processing). FIG. 13 is an example of the device import confirmation screen.

In the processing of step S201 described above, when the processing unit 220 detects that the import file F has been uploaded, the processing unit 220 reads a header section of the import file F (step S301), and determines whether the content of the header section is valid (step S302), as illustrated in FIG. 9. Here, as illustrated in FIG. 10, the import file F includes the header section and a detail section. The header section includes a plurality of header fields (for example, a file version, or the like), and the detail section includes a plurality of detailed fields (for example, a terminal ID, or the like). The processing unit 220 reads the header section in the import file F in which the file format is defined as described above, and, for example, determines whether or not a predetermined numerical value or character string is registered in the file version, whether or not the start line of the detail section corresponds to a predetermined line, and whether or not a predetermined character string is registered as a computer classification of the processing target in a function key. The computer classification is an attribute value that defines the role of a computer as an internal code. Therefore, examples of the predetermined character string registered in the function key include a character string Client indicating a client, a character string Server indicating a server, a character string Other indicating other elements, and a character string Unknown indicating unknown elements. The file format of the device information is basically the same as the file format of the import file F.

Here, in a case where a predetermined numerical value or character string is not registered in the file version, the start line of the detail section does not correspond to a predetermined line, or a predetermined character string is not registered as the processing target computer classification in the function key, the processing unit 220 determines that the content of the header section is invalid (step S302: NO). In this case, the processing unit 220 sets an error message (step S303), and returns to the processing immediately before step S101. The processing unit 220 transmits the set error message to the management terminal 100, and thus, the management terminal 100 displays the error message on the device import screen (see FIG. 6). Accordingly, the administrator can identify that there is a problem with the content of the header section.

On the other hand, in a case where a predetermined numerical value or a character string is registered in the file version, the start line of the detail section corresponds to a predetermined line, and a predetermined character string is registered as the processing target computer classification in the function key, the processing unit 220 determines that the content of the header section is valid (step S302: YES). In this case, the processing unit 220 acquires device information from the device information storage unit 210 (step S304), and sets the number of pre-execution items that is the number of items before execution (step S305). More specifically, the processing unit 220 acquires the computer classification and the computer name in the device information from the device information storage unit 210, and holds the number of pre-execution items. When the processing of step S305 is completed, the processing unit 220 starts loop processing (step S306). The loop processing is performed by the number of all terminal IDs included in the device information acquired by the processing unit 220. Instead of the terminal IDs, the number of the computer names may be used.

When the loop processing starts, the processing unit 220 first determines whether or not the computer classification in the device information matches the processing target computer classification of the header section included in the import file F (step S307). When the computer classifications do not match (step S307: NO), the processing unit 220 adds the number of items to be excluded from an application target (step S308). In other words, the processing unit 220 performs an increment of the number of items to be excluded from the application target.

On the other hand, in a case where the computer classifications match (step S307: YES), the processing unit 220 determines whether or not deletion is specified on the device import screen by the import method (step S309). Specifically, the processing unit 220 determines whether or not the selecting option 22 including deletion is selected by the import method. In a case where the deletion is specified (step S309: YES), the processing unit 220 adds the number of items of the deletion target (step S310). In other words, the processing unit 220 performs an increment of the number of items of the deletion target. On the other hand, in a case where the deletion is not specified (step S309: NO), the processing unit 220 executes the processing of step S308. That is, the processing unit 220 adds the number of items to be excluded from the application target.

When the processing of step S308 or step S310 is completed, the processing unit 220 ends the loop processing for the terminal IDs of the loop target (step S311), specifies the next terminal ID, and repeats the processing from step S307 to step S310 again. When the processing for all terminal IDs included in the device information from step S307 to step S310 is repeated, the processing unit 220 reads the detail section of the import file F (step S401), as illustrated in FIG.

11. When the processing in step S401 is completed, the processing unit 220 starts the loop processing for the detail section of the import file F (step S402). More specifically, the processing unit 220 specifies one terminal ID and executes a subsequent loop processing for the information associated with the specified terminal ID.

First, the processing unit 220 determines whether or not a first check is passed (step S403). The first check is a check on a reception form such as the number of fields of the detail section and mandatory fields. In a case where the number of fields of the detail section and mandatory fields are appropriate, the processing unit 220 determines that the first check is passed (step S403: YES).

Next, the processing unit 220 determines whether or not a second check is passed (step S404). The second check is a check on a reception form such as character length, format, and value range of the detail section. In a case where the character length, format, and value range of the detail section are appropriate, the processing unit 220 determines that the second check is passed (step S404: YES).

Next, the processing unit 220 determines whether or not a third check is passed (step S405). The third check is a check on a reception form such as a combination of network information of the detail section. That is, the processing unit 220 determines whether or not the combination of the MAC address, the Ipv4 address, and the like that have been registered as the network information is appropriate. In a case where the combination of the network information is appropriate, the processing unit 220 determines that the third check is passed (step S405: YES).

Next, the processing unit 220 determines whether or not a fourth check is passed (step S406). The fourth check is a check on a reception form such as duplication of computer names. In a case where the duplication of computer names is not present in the detail section, the processing unit 220 determines that the fourth check is passed (step S406: YES).

Next, the processing unit 220 determines whether or not a computer name that is one of the information associated with the specified terminal ID is included in the device information (step S407). In a case where the computer name is included in the device information (step S407: YES), the processing unit 220 next determines whether or not the update is specified by the import method on the device import screen (step S408). Specifically, the processing unit 220 determines whether or not the selecting option 22 including update is selected by the import method. In a case where update is not specified (step S408: YES), as illustrated in FIG. 12, the processing unit 220 adds the number of items that are normal (step S501). In other words, the processing unit 220 performs an increment of the number of items that are normal. When the processing of step S501 is completed, the processing unit 220 adds the number of items of the update target (step S502), and subtracts the number of items of the deletion target or the number of items to be excluded from the application target (step S503). In other words, the processing unit 220 performs a decrement of the number of items of the deletion target or the number of items to be excluded from the application target.

On the other hand, in a case where update is not specified (step S408: NO), the processing unit 220 adds the number of items that are abnormal (step S504). In other words, the processing unit 220 performs an increment of the number of items that are abnormal. Even in a case where the processing unit 220 determines that the first check to the fourth check are not passed in step S403 to S406 illustrated in FIG. 11 (NO in step S403, NO in step S404, NO in step S405, and NO in step S406), the processing unit 220 executes the processing of step S504 illustrated in FIG. 12. That is, the processing unit 220 adds the number of items that are abnormal.

In addition, in the processing of step S407 illustrated in FIG. 11, in a case of not being present in the device information (step S407: NO), as illustrated in FIG. 12, the processing unit 220 adds the number of items that are normal (step S505). In other words, the processing unit 220 performs an increment of the number of items that are normal. When the processing of step S505 is completed, the processing unit 220 adds the number of items of an additional target (step S506). In other words, the processing unit 220 performs an increment of the number of items of the additional target. When the processing of step S503, step S504, and step S506 is completed, the processing unit 220 ends the loop processing on the terminal ID of the loop target (step S507), specifies the next terminal ID, and repeats the processing from step S403 to step S506 again.

When the processing of step S403 to step S506 is repeated for all terminal IDs included in the import file F, the processing unit 220 sets the number of items that are scheduled after execution (step S508). When the processing of step S508 is completed, the processing unit 220 displays a device import confirmation screen (step S509). More specifically, the processing unit 220 associates the screen information regarding the device import confirmation screen with the set number of pre-execution items, the number of items that are normal, the number of items that are abnormal, the number of items of the update target, the number of items of the additional target, the number of items of the deletion target, the number of items that are excluded from the application target, and the number of the target that are scheduled after execution, and transmits the associated screen information to the management terminal 100. In this way, as illustrated in FIG. 13, the management terminal 100 displays the device import confirmation screen.

On the device import confirmation screen, the number of pre-execution items described above is displayed as the number of terminals that are currently registered. Likewise, the above-mentioned number of items that are normal is displayed as the number of items that are normally read. The above-mentioned number of items that are abnormal is displayed as the number of items that are abnormally read. The above-mentioned number of items of the update target is displayed as the number of terminals to be updated. The above-mentioned number of items of the additional target is displayed as the number of terminals to be added. The above-mentioned number of items of the deletion target is displayed as the number of terminals to be deleted. The above-mentioned number of items to be excluded from the application target is displayed as the number of terminals that are not applicable. The above-mentioned number of items that are scheduled after execution is displayed as the number of terminals after completion of import.

Then, when a specific image 31 (for example, an OK button) is indicated on the device import confirmation screen, the control unit 753 generates the instruction to update the device information and transmits the generated instruction to the information update server 200. As a result, in the processing of step S203 illustrated in FIG. 8, it is determined that the processing unit 220 has received instruction to update the device information. In contrast, when a specific image 32 (for example, a cancel button) is indicated on the device import confirmation screen, the control unit 753 generates the instruction not to update the device information, and transmits the generated instruction to the information update server 200. As a result, in the processing of step S203 illustrated in FIG. 8, it is determined that the processing unit 220 has received the instruction not to update the device information.

As described above, according to the present embodiment, the information update server 200 includes the processing unit 220. The processing unit 220 receives the import file F including the computer name of the electronic medical chart terminal 300 and the instruction to update the computer name of the electronic chart record terminal 300 as the management target stored in the device information storage unit 210 to the computer name included in the import file F. When the processing unit 220 receives the import file F and the instruction, the processing unit 220 refers to the device information storage unit 210, and acquires the computer name of the electronic medical chart terminal 300 as the management target stored in the device information storage unit 210.

Then, the processing unit 220 compares the acquired computer name of the electronic medical chart terminal 300 of the management target with the computer name of the electronic medical chart terminal 300 included in the received import file F. The processing unit 220 transmits information of the number of computer names of the electronic medical chart terminal 300 to be deleted from the device information storage unit 210 by executing update, the number of computer names of the electronic medical chart terminal 300 to be added to the device information storage unit 210 by executing update, and the number of computer names of the electronic medical chart terminal 300 included in the device information storage unit 210 both before and after execution of update, based on the comparison result. When the processing unit 220 receives the instruction to update after transmission of the information, the processing unit updates the computer name of the electronic medical chart terminal 300 as the management target stored in the device information storage unit 210 to the computer name included in the import file F. As a result, since update is performed after receiving the instruction to update after transmission of the information, it is possible to suppress erroneous update of information.

Although the preferred embodiment has been described above in detail, the embodiment is not limited to the specific embodiment, and various changes and modifications can be made within the scope of the gist of the embodiment described in the claims.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A non-transitory computer-readable recording medium storing a program that causes a computer to execute an information update process comprising:

receiving first pieces of terminal identification information and a request for updating second pieces of terminal identification information included in management targets to the first pieces of terminal identification information, the second pieces of terminal identification information being stored in a storage;

acquiring the second pieces of terminal identification information stored in the storage;

comparing the second pieces of terminal identification information with the first pieces of terminal identification information;

determining a first number of terminals to be excluded from the management targets by executing an update regarding the request, a second number of terminals to be added to the management targets by executing the update, and a third number of terminals that are included in the management targets before and after executing the update, based on a result of the comparing; and after determining the first number of terminals, the second number of terminals, and the third number of terminals, when receiving an instruction to execute the update regarding the request, updating the second pieces of terminal identification information stored in the storage to the first pieces of terminal identification information, wherein the determining process includes calculating, by using a first loop processing which reads a header of the second pieces of terminal identification information and by using a second loop processing which reads a detail section of the second pieces of terminal identification information, the first number of terminals, the second number of terminals, and the third number of terminals.

2. The recording medium according to claim 1, wherein the first number of terminals to be excluded from the management targets by executing the update is a number of terminals indicated by terminal identification information included in the second pieces of terminal identification information and not included in the first pieces of terminal identification information from among the first pieces of terminal identification information and the second pieces of terminal identification information.

3. The recording medium according to claim 1, wherein the second number of terminals to be added to the management targets by executing the update is a number of terminals indicated by terminal identification information included in the first pieces of terminal identification information and not included in the second pieces of terminal identification information from among the first pieces of terminal identification information and the second pieces of terminal identification information.

4. The recording medium according to claim 1, wherein the third number of terminals that are included in the management targets before and after executing the update is a number of terminals indicated by terminal identification information included in both of the first pieces of terminal identification information and the second pieces of terminal identification information.

5. The recording medium according to claim 1, wherein the instruction to execute the update from a first terminal is output from the first terminal when a predetermined operation is inputted on a screen displaying information.

6. The recording medium according to claim 1, wherein the program further causes the computer to execute a process comprising:

determining whether or not, based on a format, the first pieces of terminal identification information conform to the format.

7. The recording medium according to claim 6, wherein the update is executable in a case where it is determined that the first pieces of terminal identification information conform to the format based on a result of the determining.

8. An information update method executed by a computer, the method comprising:

receiving first pieces of terminal identification information and a request for updating second pieces of terminal identification information included in management targets to the first pieces of terminal identification information, the second pieces of terminal identification information being stored in a storage;

acquiring the second pieces of terminal identification information stored in the storage;

comparing the second pieces of terminal identification information with the first pieces of terminal identification information;

determining a first number of terminals to be excluded from the management targets by executing an update regarding the request, a second number of terminals to be added to the management targets by executing the update, and a third number of terminals that are included in the management targets before and after executing the update, based on a result of the comparing; and after determining the first number of terminals, the second number of terminals, and the third number of terminals, when receiving an instruction to execute the update regarding the request, updating the second pieces of terminal identification information stored in the storage to the first pieces of terminal identification information, wherein the determining process includes calculating, by using a first loop processing which reads a header of the second pieces of terminal identification information and by using a second loop processing which reads a detail section of the second pieces of terminal identification information, the first number of terminals, the second number of terminals, and the third number of terminals.

9. The information update method according to claim 8, wherein the second number of terminals to be added to the management targets by executing the update is a number of terminals indicated by terminal identification information included in the first pieces of terminal identification information and not included in the second pieces of terminal identification information from among the first pieces of terminal identification information and the second pieces of terminal identification information.

10. The information update method according to claim 8, wherein the third number of terminals that are included in the management targets before and after executing the update is a number of terminals indicated by terminal identification information included in both of the first pieces of terminal identification information and the second pieces of terminal identification information.

11. The information update method according to claim 8, wherein the instruction to execute the update from a first terminal is output from the first terminal when a predetermined operation is inputted on a screen displaying information.

12. The information update method according to claim 8, further comprising:

determining whether or not, based on a format, the first pieces of terminal identification information conform to the format.

13. The information update method according to claim 12, wherein the update is executable in a case where it is determined that the first pieces of terminal identification information conform to the format based on a result of the determining.

14. An information update device comprising:

a memory; and a processor coupled to the memory and the processor configured to:

receive first pieces of terminal identification information and a request for updating second pieces of terminal identification information included in management targets to the first pieces of terminal identification information, the second pieces of terminal identification information being stored in a storage, acquire the second pieces of terminal identification information stored in the storage, compare the second pieces of terminal identification information with the first pieces of terminal identification information, determining one of a first number of terminals to be excluded from the management targets by executing an update regarding the request, a second number of terminals to be added to the management targets by executing the update, and a third number of terminals that are included in the management targets before and after executing the update, based on a result of the comparing, and after determining the first number of terminals, the second number of terminals, and the third number of terminals, when receiving an instruction to execute the update regarding the request, update the second pieces of terminal identification information stored in the storage to the first pieces of terminal identification information, wherein the determining process includes calculating, by using a first loop processing which reads a header of the second pieces of terminal identification information and by using a second loop processing which reads a detail section of the second pieces of terminal identification information, the first number of terminals, the second number of terminals, and the third number of terminals.

* * * * *